United States Patent
Sher-Rosenthal et al.

(10) Patent No.: US 10,058,710 B2
(45) Date of Patent: Aug. 28, 2018

(54) DEVICE AND METHOD FOR REDUCING THE PERMEABILITY OF THE CORNEA

(71) Applicant: TEL HASHOMER MEDICAL RESEARCH INFRASTRUCTURE AND SERVICES LTD., Ramat Gan (IL)

(72) Inventors: Ifat Sher-Rosenthal, Shoham (IL); Ygal Rotenstreich, Kfar Bilu (IL)

(73) Assignee: Tel Hashomer Medical Research Infrastructure and Services Ltd., Ramat Gan (IL)

( * ) Notice: Subject to any disclaimer, the term of this patent is extended or adjusted under 35 U.S.C. 154(b) by 180 days.

(21) Appl. No.: 14/888,756

(22) PCT Filed: May 4, 2014

(86) PCT No.: PCT/IL2014/050401
§ 371 (c)(1),
(2) Date: Nov. 3, 2015

(87) PCT Pub. No.: WO2014/181327
PCT Pub. Date: Nov. 13, 2014

(65) Prior Publication Data
US 2016/0106996 A1     Apr. 21, 2016

(30) Foreign Application Priority Data

May 6, 2013 (IL) .......................... 226180

(51) Int. Cl.
*A61N 2/00* (2006.01)
*A61F 9/00* (2006.01)
*A61N 2/02* (2006.01)

(52) U.S. Cl.
CPC .............. *A61N 2/006* (2013.01); *A61F 9/00* (2013.01); *A61N 2/004* (2013.01); *A61N 2/02* (2013.01)

(58) Field of Classification Search
CPC .............. A61F 9/00; A61N 2/006; A61N 2/02
See application file for complete search history.

(56) References Cited

U.S. PATENT DOCUMENTS

| 5,147,284 A | 9/1992 | Fedorov et al. |
| 2009/0216068 A1* | 8/2009 | Thomas ................ A61N 2/006 600/14 |
| 2010/0130945 A1 | 5/2010 | Laniado et al. |
| 2014/0220509 A1* | 8/2014 | Vladila ................ A61C 8/0028 433/174 |

FOREIGN PATENT DOCUMENTS

| RU | 2260404 C2 | 9/2005 |
| RU | 2010138239 A | 3/2012 |

OTHER PUBLICATIONS

International Search Report for a counterpart foreign application—PCT/IL2014/050401—dated Aug. 14, 2014, 3 pages.
Written Opinion of the International Searching Authority for a counterpart foreign application—PCT/IL2014/050401—dated Aug. 14, 2014, 6 pages.
Notification of transmittal of international preliminary report on patentability for a counterpart foreign application—PCT/IL2014/050401; dated Nov. 19, 2015; 2 pages.
International preliminary report on patentability for a counterpart foreign application—PCT/IL2014/050401; dated Nov. 10, 2015; 1 page.
Written Opinion of the international searching authority for a counterpart foreign application—PCT/1L2014/050401; dated Aug. 14, 2014; 5 pages.

* cited by examiner

*Primary Examiner* — Christine H Matthews
(74) *Attorney, Agent, or Firm* — Roach Brown McCarthy & Gruber, P.C.; Kevin D. McCarthy

(57) ABSTRACT

The present invention provides a device and a method for non-invasively enhancing the integrity of the cornea by applying a magnetic field, thereby treating eye disorders.

6 Claims, No Drawings

DEVICE AND METHOD FOR REDUCING THE PERMEABILITY OF THE CORNEA

FIELD OF THE INVENTION

The present invention relates to treating eye conditions by reducing the corneal permeability by alternating magnetic field.

BACKGROUND OF THE INVENTION

The corneal epithelium functions is the principal barrier to the penetration of noxious substances into the anterior chamber, and assists in protecting the cornea by maintaining normal hydration and retaining ocular surface integrity. This diffusion barrier blocks the penetration of polarized substances such as water or ions as well as macromolecules and cells, and represents 50% of the total diffusion barrier of the healthy cornea. The corneal epithelium consists of five cell layers of stratified squamous nonkeratinized cells and an underlying basal layer. The barrier function depends on epithelial cell tight junctions, the assembly of which is regulated by intra and extra-cellular calcium. Even minor lesions of the corneal surface, too small to be recognized in the daily clinical setting, may result in impairment of the corneal epithelial barrier function that can be quantified in vivo by means of objective fluorophotometry. Corneal epithelial dysfunction may render the cornea susceptible to a variety of pathologies, including potentially hazardous bacterial or fungal infections. Several systemic and ocular conditions are associated with reduced barrier function of the cornea, thus increasing vulnerability to the above complications. An example is the diabetic population, which presents a 5-fold decrease in corneal barrier function. Aging is also associated with reduced epithelial barrier function, with an exponential increase in epithelial permeability with advanced age. A third example is the common condition keratoconjunctivitis sicca (keratitis sicca or dry eye), which causes corneal punctated epithelial lesions and increases permeation. Many types of eye drops have been developed to improve disturbed corneal epithelial surface but their efficiency is limited, and non-compliance is still a widespread problem. A possibility to decrease corneal permeability could help millions of patients suffering from mild or severe corneal barrier defects. It has been shown that exposure to magnetic fields modulates vascular tone and permeability of some tissues [see, for example, Okano H. et al.: Bioelectromagnetics 20(3)(1999)161-71]. It is therefore an object of the invention to reduce the corneal permeability by employing magnetic stimulation.

It is another object of the invention to provide a device for treating eye disorders, comprising noninvasively reducing the corneal permeability by the use of magnetic field.

It is also an object of the invention to provide a noninvasive magnetic system for eye treatment by enhancing corneal barrier function.

Other objects and advantages of present invention will appear as description proceeds.

SUMMARY OF THE INVENTION

The invention provides a magnetic device for treating an eye or eyes, comprising a generator of a changing magnetic field having a strength of from 0.1 to 5 mT in the vicinity of the eyes. Said magnetic field may be an alternating magnetic field of a frequency of from 5 Hz to 500 Hz. The magnetic field in a device of the invention is preferably generated in pulses, the signal pulses having a length of from 1 to 10 second. The magnetic field is preferably applied to the eyes in a repetitive manner; the field is created in the vicinity of an eye or eyes in repeated signal pulses. Two subsequent pulses generated by the device of the invention are preferably separated by a time interval of from 1 to 10 pulse lengths, and the total number of pulses generated by the device of the invention during a usual treatment procedure is from 10 to 100, providing the preferred total duration of the magnetic signal of from 10 to 1000 seconds.

In a preferred embodiment of the invention, provided is a magnetic device or system for treating the eyes, comprising a generator of a changing magnetic field, applied to said eyes or eye, having a strength of from 0.1 to 5 mT in the vicinity of said eyes or eye, and a frequency of from 5 Hz to 500 Hz, the field being generated in pulses having a length of from 1 to 10 second, such as 1 to 8 s, or 2 to 6 s, whereas the total duration of the pulses, which is the product of the pulse length and the pulse number, is preferably from 10 to 1000 seconds, such as 20 to 600 s, or 30 to 300 s, or 40 to 180 s, or 60 to 120 s. A magnetic device for treating the eyes according to one embodiment of the invention is configured to be worn by a subject in need of the treatment. The device for treating the eyes according to the invention has in one embodiment a form of eyeglasses. The magnetic device according to the invention is advantageously employed in treating or preventing conditions selected from the group consisting of eye dryness, keratitis sicca, corneal keratitis, corneal epithelial dysfunctions, reduced barrier function of the cornea associated with diabetes, conditions associated with increased corneal permeability due to ageing, minor lesions of the corneal surface, conditions associated with wearing contact lenses, reduced self-healing capabilities of the cornea, penetration of harmful agents to the eye from the contaminated environment, weakened anti-penetration system, and cornea-associated inflammation.

The invention provides a method of noninvasively treating an eye of a subject, comprising creating a changing magnetic field in the vicinity of the cornea of said eye, the field having a strength of from 0.1 to 5 mT, a frequency of from 5 Hz to 500 Hz, and pulse length of from 1 to 10 second, thereby reducing the corneal permeability. The total duration of the pulses, which is the product of the pulse length and the pulse number, is preferably from 10 to 1000 seconds. In a preferred embodiment of the method according to the invention, corneal permeability is reduced by the magnetic field, whereby protecting the eye against entrance of noxious agents or against loss of water. The invention provides a method of protecting the eye, comprising applying a changing magnetic field to the eye of a subject in need of the treatment, whereby reducing the corneal permeability. The method according to the invention comprises treating or preventing conditions selected from the group consisting of eye dryness, keratitis sicca, corneal keratitis, corneal epithelial dysfunctions, reduced barrier function of the cornea associated with diabetes, conditions associated with increased corneal permeability due to ageing, minor lesions of the corneal surface, conditions associated with wearing contact lenses, reduced self-healing capabilities of the cornea, penetration of harmful agents to the eye from the contaminated environment, weakened anti-penetration system, and cornea-associated inflammation.

DETAILED DESCRIPTION OF THE INVENTION

It has now been found that certain types of the magnetic field reduce the permeability of the cornea. For example, changing magnetic field of about 0.9 mT substantially reduced the permeability of compromised rabbit cornea toward fluorescein, for example when repetitively applied in 3-second pulses interrupted by 15 second intervals, repeated 36 times, at frequency of 20 Hz, one hour prior to permeability testing.

When relating to a changing magnetic field, any magnetic field which does not have constant strength and direction is comprised, including alternating or pulsed magnetic field. It is understood that changing magnetic field comprises an electric component (electromagnetic field), but mainly the strength of the magnetic component is related to in the present invention.

The alternating magnetic field can induce electric fields in tissues [P. J. Maccabee et al.: J.Clin. Neurophysiol. 8(1) (1991) 38-55], it may affect cells growth, it may modulate vascular tone and permeability by modulating calcium channels in vascular smooth muscle cells [Okano H. et al.: Bioelectromagnetics 20(3) (1999) 161-71]. Determination of potential mechanisms involved in this physiological responses to magnetic field exposure is ongoing, and multiple and variable biological mechanisms have been suggested. Magnetic field has been also used in repetitive trans-cranial magnetic stimulation, which is a process in which excitable human brain tissue is activated with an electric field induced by a changing magnetic field, and the technology has been known for over 40 years as a reversible, localized, and noninvasive treatment in various psychiatric disorders. Repetitive Magnetic Stimulation (rMS) is based on creating alternating magnetic fields by brief electric currents transmitted through an insulated coil. The present invention aims at utilizing rMS electromagnetic pulses, similar as in repetitive transcranial magnetic stimulation, for affecting the corneal tissue and reducing the corneal permeability.

The magnetic field employed in a system according to the present invention includes electromagnetic field of which magnetic component has a strength of from 0.1 to 5 mT, such as from 0.1 to 2.5 mT, or from 0.1 to 2 mT, or from 0.2 to 2.0 mT, for example around 1 mT. Said strength is considered in the vicinity of the eye to be treated, which usually includes the distance of from 0 and about 5 cm, such as from about 0.5 to about 2.5 cm, similar to the distance of the eyeglasses from the eye surface. The magnetic field may be an alternating field or pulsed field having a frequency between 5 to 500 Hz, such as 20 Hz. The field is preferably applied repetitively, comprising signal pulses of between 1 and 10 s, such as 3 s, separated by intervals having from 1 to 10 signal pulse lengths, such as 5, the total treatment time being usually between 1 and 60 minutes, such as between 2 and 20 minutes, or between 3 and 15 minutes, or between 4 and 12 minutes, for example up to about 20 minutes, or up to about 15 minutes, or up to about 12 minutes, or up to about 10 minutes, or up to about 6 minutes.

The invention provides, in one embodiment, a device that can be worn by a person, in which a magnetic field generator is incorporated. The device may have a form similar to regular eyeglasses. The generator can generate a magnetic field of different parameters. The magnetic field reaches the eye. The decrease of the corneal permeability protects the cornea from physical damages, for example in persons suffering from eye dryness. In one embodiment of the invention, the magnetic field will be generated by a special contact lens.

Certain magnetic stimulations decrease the permeability of the cornea, beneficially affecting persons suffering from eye dryness or persons wearing contact-lenses, leading to decreased lubrication of the eye, known to make the cornea more susceptible to different types of damages. It has been found by the inventors that repetitive magnetic stimulation reduces the corneal permeability as desired. For example, changing magnetic field which has a frequency of 5-500 Hz, such as 10-100 Hz, for example 20 Hz, and which has an intensity of 0.1-5 mT, such as 0.2-4 mT or 0.3-3 mT, or 0.4-2 mT, for example about 1 mT, enhances the corneal integrity and so protects the eye from damages eventually caused by undesired entry of damaging agents from the environment and/or undesired exit of eye liquids.

This invention provides a device, a method, and a system for reducing the corneal penetrability by applying magnetic field, assisting clinicians and pharmacologists challenged by eye disorders in which the entrance of noxious factors cannot be efficiently controlled. The invention enables to treat or to prevent or to mitigate the conditions selected from the group consisting of eye dryness, keratitis sicca, corneal keratitis, corneal epithelial dysfunctions, reduced barrier function of the cornea associated with diabetes, conditions associated with increased corneal permeability due to ageing, minor lesions of the corneal surface, conditions associated with wearing contact lenses, reduced self-healing capabilities of the cornea, penetration of harmful agents to the eye from the contaminated environment, weakened anti-penetration system, and cornea-associated inflammation. The conditions to be handled by the device and method of the invention may be associated with items selected from the group consisting of keratitis caused be contact lenses, epidemic keratoconjunctivitis, aging of the cornea, epithelial corneal dystrophies, atopic keratoconjunctivitis, vernal keratoconjunctivitis, allograft corneal epithelial rejection, limbal chemical burn, epithelial keratitis—herpes simplex, epithelial keratitis—neurotropic, Sjogren's syndrome, tear production induced by anti-Parkinson agents or anti-spasmotic agents or antiulcer-agents or aqueous tear deficiency medication, staphylococcal belephritis, argon laser burns, Reiter syndrome, rheumatoid peripheral ulcerative keratitis, and systemic diseases.

In exemplifying some embodiments of the invention, ocular penetration of sodium-fluorescein in rabbit eyes following magnetic stimulation at different intensities was used. The model using rabbit eyes and sodium fluorescein was employed by the inventors due to the high ocular safety profile of the compound, its hydrophilic nature, and the fact that its concentration in the anterior chamber can be measured with good precision and reproducibility using a fluorometer. The baseline corneal permeability of this hydrophilic substance is very limited, due to the corneal barrier function. It is known that fluorescein does not penetrate or stain live corneal epithelial cells upon topical application, the corneal epithelial defects are readily stained as the dye diffuses between cells into the adjacent intercellular spaces and penetrates into the underlying corneal stroma. Rabbits were either non treated (sham) or treated with repeated magnetic stimulation (rMS) at different intensities one hour prior to fluorescein application. Fluorescence measurements of anterior chamber fluid was used to quantify the ocular penetration. In order to demonstrate the safety of the procedure, animals were tested for retinal function by electroretinogram prior to rMS treatment, at 1 day, 1 week, and 1 month following the treatment. Moreover, animals were examined by histological analysis for possible adverse effects on retinal structure.

The invention enables to enhance the corneal integrity. Ocular surface disease comprises numerous disorders affecting millions around the world, and is a problem encountered routinely in daily practice. A subgroup of these patients suffers from a chronic compromise of the corneal surface, which in turn may result in corneal scarring, infection, thinning and ultimately perforation. In this subgroup, the self healing capabilities of the cornea are significantly impaired in comparison to normal corneas. A method for enhancing corneal integrity and reducing permeability may serve to help protect these compromised corneas, and may even facilitate accelerated healing. The invention enables to reduce the permeability in cornea subjected to magnetic stimulation, so safeguarding the ocular surface in these delicate situations. To gain insight on the mechanisms underlying rMS corneal effects, the possibility that rMS enhances epithelial recovery was checked, including monitoring the corneal erosion area in sham and rMS treated animals. Without wishing to be bound by any theory, the inventors assume that the alternating magnetic field which was employed acts both directly and also through the induced electrical field, affecting both ions and dipoles on the molecular level, as well as the whole cells.

The invention provides a magnetic system and device comprising a generator of changing magnetic field, enabling repetitive magnetic stimulation, having a strength of from 0.1 mT to 5 mT and a frequency of from 5 Hz to 500 Hz, the field generated in pulses having a length of from 1 to 20 second, separated by intervals of from 1 to 30 second. The term "strength" in regard to the magnetic field is used in the same sense as the term "intensity", intending the field magnitude measured in the units of tesla (T). The system and device of the invention employ, in some embodiments, magnetic field of 0.1-10 mT, for example 0.1-5 mT, or 0.2-4 mT, or 0.3-3 mT, or 0.5-2 mT. The system and device of the invention employ, in some embodiments, alternating magnetic field of 5-500 Hz, for example 10-250 Hz, or 10-100 Hz, or 10-50 Hz. The system and device of the invention employ, in some embodiments, alternating magnetic field in pulses having duration 1-100 s, for example 1-20 s, or 2-20 s, or 2-10 s. The system and device of the invention employ, in some embodiments, alternating magnetic field in pulses separated by time intervals without signal of the same length as the pulse duration or more, for example an interval twice as long as the pulse duration, or three times as long as the pulse duration, or four times as long as the pulse duration, or five times as long as the pulse duration, or from six times to ten times as long as the pulse duration.

The system and device of the invention enable a noninvasive eye treatment by enhancing the corneal barrier function.

In a preferred embodiment, the system and device of the invention assist in protecting the cornea by maintaining normal hydration and retaining ocular surface integrity via reducing the corneal permeability.

The invention will be further described and illustrated in the following examples.

EXAMPLES

Materials and Methods

Animals—Twenty New Zealand white rabbits, an outbred stock used in dermatological, ophthalmological and other areas of biomedical research. Animals were housed at the Glodschlager Eye Research Institute animal facility.

Compromised corneal epithelium was achieved by anesthetizing animals with xylazine-ketamine and keeping their eyes open for 90 minutes. Clinical signs of dry eye can be observed after this time period in the form of acute desiccation.

Dye application and anterior chamber tap—5 microliter of 10% sodium fluorescein was instilled on rabbit corneas pre-evaluated for the absence of epithelial damage using a slit-lamp. After 30 seconds of residence time on the ocular surface, the eye was washed out thoroughly using normal saline for 5-7 minutes or more as needed. Taps (100 µl) were taken from the anterior chambers of the rabbit eyes at predetermined intervals during 60 minutes after instillation of the fluorescein. For rose bengal staining, 0.5% solution was used.

Fluorometry measurement—using a fluorometer (FL×800 Fluorescence Microplate Reader, BioTek) the anterior chamber fluid was analyzed for fluorescein concentration at wavelengths of 485/20 (excitation) and 528/20 (emission).

Magnetic stimulation—rMS (repeated magnetic stimulation) was applied to one eye pre-evaluated for the absence of epithelial damage. The eye was exposed to single session of rMS at varying output intensities (0 to 1 mT), 20 Hz stimulus for 3 seconds, followed by a 15 second interval with no stimulus (no signal). This was repeated 36 times. Following the above repetitive stimulation, fluorescein was instilled and anterior chamber fluid analyzed.

Electroretinogram (ERG)—Retinal function of all the animals was tested prior to rMS treatment, and at one day, one week and one month after treatment. Animals was dark-adapted for a minimum of 6 hours prior to ERG measurements. Animals were anesthetized with intraperitoneal Ketamine and Xylazine. Pupils were dilated with topical 1% tropicamide. The corneas were kept moist with 2.5% hydroxypropyl methylcellulose. Body temperature were kept at 37° C. with a heating pad. ERGs were recorded from both eyes simultaneously using golden wire loops on the corneas, in five increasing intensities (−20, −10, 0, +2.5, +10 dB). A chloride silver reference electrode was placed subcutaneously near the temporal eye corner. The ground electrode was placed on the tail. Scotopic ERG responses was averaged with stimulus intervals of 1 to 30 seconds depending on intensity, and 20 photopic responses were averaged with stimulus intervals of 1 second. Animals was light-adapted for 5 minutes before photopic recordings.

Histology—Two rabbits were sacrificed and their eyes fixed in 3.7% formaldehyde for 24 hrs and embedded in paraffin. Paraffin sections were stained with hematoxylin and eosin, and examined for eye morphology.

Example 1

500 µg sodium fluorescein was introduced onto rabbit corneas with intact or compromised epithelia, followed by withdrawing anterior chamber taps at different time intervals after washout. A cornea with a compromised epithelium was defined as one with any sign of staining immediately after initial washout of the dye. The erosions seen in our preliminary study varied slightly in size (⅕-⅓ of corneal surface); however, no significant variations in permeability were noted. The fluorescein concentration in the anterior chamber increased with time, with a peak at 60 min post application. Moreover, fluorescein concentration in the anterior chamber was significantly higher, by up to 100 fold, in eyes with compromised epithelium. The concentration of fluorescein found in the anterior chamber during the different time intervals after washout presented similar dynamics to those found in a study on human eyes comparing normal to patients with corneal damage and increased epithelial permeability [Matsuo H. et al.: Am. J. Ophthalmol. 140(4) 2005) 742-4].

The effects of magnetic stimulation on corneal penetration were checked in rabbits treated in one eye with rMS at 940 µT, 20 Hz, 36 repeats 1 hr prior to fluorescein application. The rabbit Motor Threshold was at 890 µT (microtesla). Hence an intensity higher than the motor threshold was chosen. Magnetic stimulation at 940 µT significantly reduced fluorescein penetration in eyes with compromised epithelium to a level similar to that obtained in eyes with intact epithelium. These findings demonstrate that rMS treatment can minimize barrier defects arising from epithelial erosion, suggesting that rMS may be used for treatment in patients with compromised corneal epithelium.

Example 2

500 µg sodium fluorescein was introduced onto rabbit corneas with intact or compromised epithelia, followed by withdrawing anterior chamber taps at different time intervals after washout. Rabbits, either sham or rMS treated at different intensities, 1 h prior to fluorescein application were divided to 4 groups (N=5 in each): Group A received sham treatment; groups B, C and D magnetic stimulation at 760, 890 and 940 microtesla, respectively. The fluorescence measurements values were averaged in each group. The fluorescence average values in groups B, C, and D were about 110%, 50%, and 20%, respectively, relatively to A.

The effect of rMS on corneal damage was histopathologically examined. Corneal specimens were stained with hemotoxylin and eosin. In non-treated dry eye, local erosion of several epithelial cell layers was observed, whereas the histological structures of the posterior stromal cell layer and the basement membrane remained intact. By contrast, in eyes pretreated with rMS, corneas were demonstrated to have the stromal cell layer uniformly overlaid with intact multilayered epithelium.

Further, to evaluate how long the therapeutic effect of rMS lasts, three rabbits were treated with rMS on one eye as indicated above. Three weeks after a single rMS session, dry eye was induced in both eyes the rabbits, and fluorescein concentration in the anterior chambers tap were measured 60 minutes after application of fluorescein. Significantly reduced fluorescein penetration was observed in the treated eyes, compared to the non-treated ones.

To evaluate safety of rMS treatment, fifteen rabbits were monitored for up to six months following rMS treatment. No adverse effects on general health, body weight, or cataract development were found in any animal. In addition, eyes removed five hours and 3 months, respectively, after rMS treatment were analyzed by histopathology, and no adverse effects were found in any eye; specifically retinal structures were undistinguishable in the two eyes and in untreated control eyes, when checked on paraffin sections stained with hematoxylin and eosin, or with Giemsa stain.

The findings demonstrated that the rMS treatment according to the invention can minimize barrier defects arising from dry eye for at least three weeks in mammals, with no adverse effects, suggesting that rMS may be advantageously used for treating patients suffering from dry eye.

While this invention has been described in terms of some specific examples, many modifications and variations are possible. It is therefore understood that within the scope of the appended claims, the invention may be realized otherwise than as specifically described.

The invention claimed is:

1. A method of treating an eye of a subject, comprising i) applying a changing magnetic field; ii) measuring penetration of fluorescein from the corneal surface to anterior chamber of said eye; and iii) selecting a magnetic field strength sufficient to reduce corneal permeability.

2. The method of claim 1, wherein the corneal permeability is reduced by the magnetic field, thereby protecting the eye against entrance of noxious agents or against loss of water.

3. The method of claim 1, comprising repetitively applying said magnetic field to the eye of said subject in need of said treating, thereby reducing the corneal permeability.

4. The method of claim 1, comprising treating or preventing conditions selected from the group consisting of keratitis sicca, eye dryness, corneal epithelial dysfunctions, corneal keratitis, reduced barrier function of the cornea associated with diabetes, conditions associated with increased corneal permeability due to ageing, minor lesions of the corneal surface, conditions associated with wearing contact lenses, reduced self-healing capabilities of the cornea, and penetration of harmful agents to the eye from a contaminated environment.

5. The method of claim 1, wherein said strength is sufficient to reduce the corneal permeability as measured by the penetration of fluorescein from the corneal surface to the anterior chamber.

6. The method of claim 1, comprising treating eye dryness.

* * * * *